(12) United States Patent
Gunnarsson et al.

(10) Patent No.: US 11,270,788 B2
(45) Date of Patent: Mar. 8, 2022

(54) WELLNESS SUPPORT GROUPS FOR MOBILE DEVICES

(71) Applicant: Noom, Inc., New York, NY (US)

(72) Inventors: Ketill Gunnarsson, Vienna (AT); Thomas Patrick Joynt, Brooklyn, NY (US); Viktor Braut, Krk (HR); Diana Mackinnon, New York, NY (US); Zrinka Gavran, Zagreb (HR); Stacy Sami Lee, New York, NY (US); Artem Petakov, New York, NY (US); Ken Nesmith, New York, NY (US); Astha Gupta, Brooklyn, NY (US); Thomas Payne, New York, NY (US); Christos Avgerinos, New York, NY (US); Vera Kern, New York, NY (US); Mark Simon, New York, NY (US); Yun Eui So, New York, NY (US); Betina Evancha, New York, NY (US); William Avery Ginsberg, Chappaqua, NY (US); Nathan Ie, Boston, MA (US); Matt Sonier, New York, NY (US); Jesse Sae-ju Jeong, West New York, NJ (US); Thomas Benjamin Hildebrandt, New York, NY (US); Charlie Sneath, New York, NY (US); Gennadiy Shafranovich, Brooklyn, NY (US)

(73) Assignee: Noom, Inc., New York, NY (US)

( * ) Notice: Subject to any disclaimer, the term of this patent is extended or adjusted under 35 U.S.C. 154(b) by 0 days.

(21) Appl. No.: 15/976,699

(22) Filed: May 10, 2018

(65) Prior Publication Data
US 2018/0262584 A1    Sep. 13, 2018

Related U.S. Application Data

(63) Continuation of application No. 14/242,600, filed on Apr. 1, 2014, now Pat. No. 9,992,292.

(51) Int. Cl.
*G16H 20/60* (2018.01)
*H04L 67/50* (2022.01)
(Continued)

(52) U.S. Cl.
CPC ............. *G16H 20/60* (2018.01); *G06Q 10/10* (2013.01); *G06Q 10/109* (2013.01);
(Continued)

(58) Field of Classification Search
CPC ........ H04L 67/22; G16H 20/60; G16H 20/00; G06Q 10/10; G06Q 10/0637; G09B 19/00
(Continued)

(56) References Cited

U.S. PATENT DOCUMENTS

| 5,586,252 A | 12/1996 | Barnard et al. |
| 5,796,393 A | 8/1998 | MacNaughton et al. |

(Continued)

FOREIGN PATENT DOCUMENTS

| JP | 2008-505393 A | 2/2008 |
| JP | 2015197908 A | 11/2015 |

(Continued)

OTHER PUBLICATIONS

Acobgyn, "Definition Of Wellness—Key Dimensions For Optimum Health", 2006 (Year: 2006).*

(Continued)

*Primary Examiner* — Ondrej C Vostal
(74) *Attorney, Agent, or Firm* — Schwegman Lundberg & Woessner, P.A.

(57) ABSTRACT

A method of managing an online support group to increase the odds that users will attain their wellness goals is disclosed. A request from a user to join a support group is received. A preference of the user with respect to a type of the support group is received. The support group is selected from a plurality of support groups based on the preference (Continued)

of the user and a preference of a member of the support group. Based on an acceptance by the user of an option to join the support group, the plurality of support groups is reorganized.

20 Claims, 19 Drawing Sheets

(51) Int. Cl.
  *H04L 67/306* (2022.01)
  *G06Q 10/10* (2012.01)
  *G16H 40/67* (2018.01)
(52) U.S. Cl.
  CPC ............ *G16H 40/67* (2018.01); *H04L 67/22* (2013.01); *H04L 67/306* (2013.01)
(58) Field of Classification Search
  USPC ........................................................ 709/204
  See application file for complete search history.

(56) References Cited

U.S. PATENT DOCUMENTS

| | | | |
|---|---|---|---|
| 6,018,716 A | 1/2000 | Denardo et al. | |
| 6,029,195 A * | 2/2000 | Herz | G06Q 30/02 725/116 |
| 6,039,688 A | 3/2000 | Douglas et al. | |
| 6,094,687 A * | 7/2000 | Drake, Jr. | H04L 49/3081 709/241 |
| 6,817,863 B2 | 11/2004 | Bisogno | |
| 7,124,164 B1 * | 10/2006 | Chemtob | G06Q 10/10 709/204 |
| 7,413,438 B2 | 8/2008 | Bisogno | |
| 7,478,129 B1 | 1/2009 | Chemtob et al. | |
| 7,886,023 B1 * | 2/2011 | Johnson | H04L 67/1002 709/219 |
| 8,073,731 B1 * | 12/2011 | Rajasenan | G06Q 10/0637 705/7.38 |
| 8,170,465 B2 * | 5/2012 | Griffin | G06Q 10/06311 434/350 |
| 8,239,246 B1 | 8/2012 | Bigham et al. | |
| 8,348,809 B2 | 1/2013 | Van Der Zande et al. | |
| 8,693,416 B2 * | 4/2014 | Zheng | H04B 7/0452 370/329 |
| 8,856,233 B2 * | 10/2014 | Lacapra | G06F 17/30206 709/204 |
| 9,037,578 B2 | 5/2015 | Brust et al. | |
| 9,483,512 B2 * | 11/2016 | Schreter | G06F 16/221 |
| 2002/0087678 A1 * | 7/2002 | Padilla | H04L 29/06 709/223 |
| 2002/0174050 A1 | 11/2002 | Eynard et al. | |
| 2002/0178017 A1 * | 11/2002 | Stevens | G06Q 10/10 705/35 |
| 2002/0194015 A1 * | 12/2002 | Gordon | G06F 16/273 705/1.1 |
| 2003/0028595 A1 | 2/2003 | Vogt et al. | |
| 2003/0041109 A1 * | 2/2003 | Meloni | G06Q 10/10 709/205 |
| 2004/0023726 A1 * | 2/2004 | Ritson | A63B 23/12 473/220 |
| 2004/0153506 A1 * | 8/2004 | Ito | H04L 67/24 709/204 |
| 2004/0177158 A1 * | 9/2004 | Bauch | H04L 29/06 709/245 |
| 2004/0260701 A1 | 12/2004 | Lehikoinen et al. | |
| 2004/0267565 A1 * | 12/2004 | Grube | G06Q 50/22 705/2 |
| 2005/0010640 A1 | 1/2005 | Cannata et al. | |
| 2005/0114759 A1 | 5/2005 | Williams et al. | |
| 2005/0232401 A1 | 10/2005 | Ordille et al. | |
| 2005/0240434 A1 * | 10/2005 | Wooten | G06F 19/3475 705/2 |
| 2005/0254665 A1 * | 11/2005 | Vaudrey | G10K 11/178 381/72 |
| 2005/0288996 A1 | 12/2005 | Wallman et al. | |
| 2006/0064322 A1 * | 3/2006 | Mascarenhas | G06Q 10/10 705/2 |
| 2006/0190303 A1 | 8/2006 | Yourist et al. | |
| 2006/0248350 A1 * | 11/2006 | Stanev | H04L 67/1097 713/189 |
| 2007/0055756 A1 * | 3/2007 | Richards | F24F 11/30 709/223 |
| 2007/0133428 A1 * | 6/2007 | Taylor | H04L 45/308 370/252 |
| 2007/0208802 A1 * | 9/2007 | Barman | G06F 3/04842 709/203 |
| 2007/0253545 A1 | 11/2007 | Chatterjee et al. | |
| 2008/0052203 A1 | 2/2008 | Beyer et al. | |
| 2008/0109412 A1 | 5/2008 | Drayer et al. | |
| 2008/0126309 A1 * | 5/2008 | Rowley | H04L 61/1552 |
| 2008/0155070 A1 * | 6/2008 | El-Damhougy | H04B 7/18584 709/220 |
| 2008/0222055 A1 | 9/2008 | Hughes | |
| 2008/0241810 A1 * | 10/2008 | Flores | G09B 5/00 434/350 |
| 2008/0253378 A1 * | 10/2008 | Curry | G06Q 30/00 370/395.4 |
| 2008/0256069 A1 | 10/2008 | Eder et al. | |
| 2008/0270363 A1 | 10/2008 | Hunt et al. | |
| 2009/0006127 A1 | 1/2009 | Bahar | |
| 2009/0071857 A1 | 3/2009 | Astwood et al. | |
| 2009/0222551 A1 | 9/2009 | Neely et al. | |
| 2009/0269728 A1 * | 10/2009 | Verstegen | A63B 21/00196 434/247 |
| 2009/0299761 A1 * | 12/2009 | Thakur | G06Q 10/10 705/2 |
| 2010/0114606 A1 * | 5/2010 | Snyder | G06Q 10/06 705/3 |
| 2010/0153453 A1 | 6/2010 | Knowles et al. | |
| 2010/0161709 A1 | 6/2010 | Fourman | |
| 2010/0185654 A1 * | 7/2010 | Fortuna | G06F 16/93 707/769 |
| 2010/0205542 A1 | 8/2010 | Walman | |
| 2010/0295685 A1 * | 11/2010 | Parvin | G16H 40/20 340/573.1 |
| 2011/0029622 A1 | 2/2011 | Walker et al. | |
| 2011/0066425 A1 * | 3/2011 | Hudgins | G06Q 10/10 704/10 |
| 2011/0119212 A1 * | 5/2011 | De Bruin | A61B 5/00 706/12 |
| 2011/0258179 A1 * | 10/2011 | Weissman | G06F 16/24544 707/714 |
| 2012/0010867 A1 | 1/2012 | Eder | |
| 2012/0023107 A1 * | 1/2012 | Nachnani | G06F 16/24532 707/748 |
| 2012/0023163 A1 | 1/2012 | Mangold | |
| 2012/0059668 A1 * | 3/2012 | Baldock | G06Q 10/10 705/3 |
| 2012/0129145 A1 | 5/2012 | Miller et al. | |
| 2012/0131104 A1 | 5/2012 | Beaven et al. | |
| 2012/0143013 A1 * | 6/2012 | Davis, III | A61B 5/0002 600/300 |
| 2012/0143663 A1 * | 6/2012 | Miller | G06Q 30/0212 705/14.14 |
| 2012/0173445 A1 * | 7/2012 | Asaimuthu | G06Q 10/06 705/321 |
| 2012/0179980 A1 | 7/2012 | Whalin et al. | |
| 2012/0182384 A1 | 7/2012 | Anderson et al. | |
| 2012/0208634 A1 | 8/2012 | Cohen et al. | |
| 2012/0209856 A1 * | 8/2012 | Mckee | G06Q 10/101 707/748 |
| 2012/0239739 A1 * | 9/2012 | Manglik | G06F 9/5077 709/203 |
| 2012/0244504 A1 | 9/2012 | Wasserman | |
| 2012/0308975 A1 | 12/2012 | Hsiao et al. | |
| 2013/0017528 A1 * | 1/2013 | Nguyen | G06Q 50/20 434/362 |
| 2013/0018960 A1 * | 1/2013 | Knysz | H04L 65/403 709/204 |

(56) References Cited

U.S. PATENT DOCUMENTS

| | | | |
|---|---|---|---|
| 2013/0031475 A1* | 1/2013 | Maor | G06Q 10/10 715/706 |
| 2013/0046548 A1 | 2/2013 | Snider et al. | |
| 2013/0091001 A1* | 4/2013 | Jia | G06Q 30/0224 705/14.25 |
| 2013/0091214 A1 | 4/2013 | Kellerman et al. | |
| 2013/0132866 A1 | 5/2013 | Shafique | |
| 2013/0196822 A1* | 8/2013 | Watterson | G06F 19/3481 482/9 |
| 2013/0216982 A1 | 8/2013 | Bennett et al. | |
| 2013/0226708 A1* | 8/2013 | Good | G06Q 10/101 705/14.66 |
| 2013/0232263 A1* | 9/2013 | Kelly | G06F 16/285 709/224 |
| 2013/0261776 A1* | 10/2013 | Cardoso, Jr. | A63B 24/0062 700/91 |
| 2013/0339449 A1* | 12/2013 | Morin | G06Q 10/10 709/204 |
| 2014/0025767 A1 | 1/2014 | De Kezel et al. | |
| 2014/0042092 A1* | 2/2014 | Akonur | A61M 1/1619 210/646 |
| 2014/0067970 A1 | 3/2014 | Sharma | |
| 2014/0074264 A1 | 3/2014 | Anderson et al. | |
| 2014/0085077 A1 | 3/2014 | Luna et al. | |
| 2014/0108066 A1* | 4/2014 | Lam | G06Q 10/02 705/5 |
| 2014/0149165 A1* | 5/2014 | Husby | G06Q 10/1095 705/7.19 |
| 2014/0172461 A1* | 6/2014 | Rogers | G06Q 10/10 705/3 |
| 2014/0181267 A1* | 6/2014 | Wadkins | H04L 69/163 709/219 |
| 2014/0230076 A1* | 8/2014 | Micucci | G06F 21/6209 726/28 |
| 2014/0276244 A1 | 9/2014 | Kamyar | |
| 2014/0278513 A1 | 9/2014 | Prakash et al. | |
| 2014/0310013 A1 | 10/2014 | Ram et al. | |
| 2014/0344356 A1 | 11/2014 | Ramadhan | |
| 2014/0372159 A1* | 12/2014 | Bain | G06Q 10/0631 705/7.12 |
| 2015/0079561 A1* | 3/2015 | Petakov | G06Q 10/10 434/236 |
| 2015/0133812 A1* | 5/2015 | deCharms | A61B 5/4824 600/559 |
| 2015/0161336 A1* | 6/2015 | Kalathil | G06Q 50/24 705/3 |
| 2015/0187226 A1* | 7/2015 | Slovenski | G09B 19/00 434/247 |
| 2015/0281384 A1 | 10/2015 | Gunnarsson et al. | |
| 2015/0363481 A1* | 12/2015 | Haynes | G06Q 10/10 707/748 |
| 2016/0035248 A1 | 2/2016 | Gibbs | |
| 2016/0088075 A1* | 3/2016 | Barman | G06F 3/04842 709/204 |
| 2016/0246936 A1* | 8/2016 | Kahn | H04L 67/12 |

FOREIGN PATENT DOCUMENTS

| | | |
|---|---|---|
| KR | 1020150114354 A | 10/2015 |
| KR | 102197458 | 1/2021 |

OTHER PUBLICATIONS

Merriam-Webster, "function", 2018 (Year: 2018).*
Merriam-Webster, "suboptimal", 2018 (Year: 2018).*
Merriam-Webster, "cluster", 2020 (Year: 2020).*
Dictionary.com, "statistics", 2021 (Year: 2021).*
Merriam-Webster dictionary, "statistics", 2021 (Year: 2021).*
Iamnitchi et al., "Interest-Aware Information Dissemination in Small-World Communities", 2005 (Year: 2005).*
Mackin et al., "Adopting NoSQL Databases Using a Quality Attribute Framework and Risk Analysis", 2016 (Year: 2016).*
Maria-Iuliana et al., "Platform for Creating Collaborative E-learning Communities based on Automated Composition of Learning groups", 2013 (Year: 2013).*
Quora, "caching layer", 2021 (Year: 2021).*
Romano et al., "User Driven Design of a Web-Based group Support System", 1997 (Year: 1997).*
SAP, "Using JAP in the Persistence Layer", 2021 (Year: 2021).*
Wikipedia, "ACID", 2021 (Year: 2021).*
U.S. Appl. No. 14/242,600, Corrected Notice of Allowance dated Feb. 8, 2018, 5 pgs.
U.S. Appl. No. 14/242,600, Final Office Action dated Aug. 5, 2016, 17 pgs.
U.S. Appl. No. 14/242,600, Non Final Office Action dated Feb. 2, 2016, 21 pgs.
U.S. Appl. No. 14/242,600, Notice of Allowance dated Jan. 17, 2018, 21 pgs.
U.S. Appl. No. 14/242,600, Notice of Allowance dated Jun. 15, 2017, 14 pgs.
U.S. Appl. No. 14/242,600, Response filed May 2, 2016 to Non Final Office Action dated Feb. 2, 2016, 14 pgs.
U.S. Appl. No. 14/242,600, Response filed Nov. 7, 2016 to Final Office Action dated Aug. 5, 2016, 14 pgs.
Case 2:16-cv-01225-RWS-RSP, Civil Cover Sheet filed Nov. 3, 2016, (Nov. 3, 2016), 2 pgs.
Case 2:16-cv-01225-RWS-RSP, Final Judgment filed Dec. 21, 2016, (Dec. 21, 2016), 1 pg.
Case 2:16-cv-01225-RWS-RSP, Jury Trial Demanded and Complaint for Patent Infringement, filed Nov. 3, 2016, (Nov. 3, 2016), 14 pgs.
Case 2:16-cv-01225-RWS-RSP, Jury Trial Demanded and Corporate Disclosure Statement filed Nov. 3, 2016, (Nov. 3, 2016), 1 pg.
Case 2:16-cv-01225-RWS-RSP. Motion to Dismiss with Prejudice filed Dec. 21, 2016. (Dec. 21, 2016), 2 pgs.
Case 2:16-cv-01225-RWS-RSP, Order filed Jan. 19, 2017, (Jan. 19, 2017), 1 pg.
Case 2:16-cv-01225-RWS-RSP, Proposed Order filed Dec. 21, 2016, (Dec. 21, 2016), 2 pgs.
Case 2:16-cv-01225-RWS-RSP, Referral Order RS-72-1, Document 4 filed Nov. 3, 2016, (Nov. 3, 2016), 2 pgs.
Case 2:16-cv-01225-RWS-RSP, Report on the Filing or Determination of an Action Regarding a Patent or Trademark filed Jan. 19, 2017, (Jan. 19, 2017), 1 pg.
Case 2:16-cv-01225-RWS-RSP, Report on the Filing or Determination of an Action Regarding a Patent or Trademark filed Nov. 3, 2016, (Nov. 3, 2016), 1 pg.
Case 2:16-cv-01225-RWS-RSP, Summons in a Civil Action filed Nov. 3, 2016, (Nov. 3, 2016), 2 pgs.
Case 2:16-cv-01225-RWS-RSP, Summons in a Civil Action filed Nov. 9, 2016, (Nov. 9, 2016), 2 pgs.
Case 2:16-cv-01225-RWS-RSP, Unopposed Application for Extension of Time to Answer Complaint filed Nov. 23, 16, (Nov. 23, 2016), 1 pg.
Definition of "Wellness"—Key Dimensions of Optimum Health, Atlantic Cape OB/GYN, (2006).
European Application Serial No. 14275097.5, Extended European Search Report dated Sep. 18, 2014, 5 pgs.
European Application Serial No. 14275097.5, Response filed Apr. 7, 2016 to Extended European Search Report dated Sep. 18, 2014, 8 pgs.
"Nutrition", Merriam-Webster, (2017).
Tyran, et al., "The Application of Electronic Meeting Technology to Support Strategic Management", (1992).
Korean Application Serial No. 10-2014-0057148, Notice of Preliminary Rejection dated May 29, 2020, 6 pgs.
Korean Application Serial No. 10-2014-0057148, Response filed Jul. 29, 2020 to Notice of Preliminary Rejection dated May 29, 2020, w/ English Translation, 36 pgs.
"Korean Application Serial No. 10-2020-0183130, Notice of Preliminary Rejection dated Apr. 22, 2021", w/ English Translation, 14 pgs.

* cited by examiner

FIG. 11

WELLNESS SUPPORT GROUPS FOR MOBILE DEVICES

CROSS-REFERENCE TO RELATED APPLICATIONS

This application is a continuation of prior application Ser. No. 14/242,600, filed on Apr. 1, 2014, which is incorporated by reference herein in its entirety.

BACKGROUND

Various issues may prevent people from participating in or taking full advantage of physical support groups. Such issues may relate to the time at which the group meets not fitting the user's schedule, the location of the meeting not being convenient to the user (e.g., based on an amount of travel), the participants not being a good match for the user in terms of goals sought, progress toward goals attained, or other factors, and so on. Furthermore, existing online support groups may lack a structure or means of facilitation that approximates what the user would find in physical support groups.

BRIEF DESCRIPTION OF THE DRAWINGS

FIG. 7-18 are screenshots of example user interfaces to allow the user to interact with the online support groups.

DETAILED DESCRIPTION

In the following description, for purposes of explanation, numerous specific details are set forth in order to provide an understanding of various embodiments of the present subject matter. It will be evident, however, to those skilled in the art that various embodiments may be practiced without these specific details.

In various embodiments, a method of helping users attain their goals is disclosed. The method includes creating online support groups, selecting online support groups for users, and providing mechanisms to allow the users to interact with the online support groups, provide facilitation of the online support groups, and receive facilitation of the online support groups. In various embodiments, operations occur on the client or the server, with some executed by humans, and some executed automatically or with algorithmic guidance. In this description we present one example embodiment of the client-server split.

In various embodiments, an online support group for a user of a wellness application may be selected based on various criteria, such as how well the user is likely to fit into a dynamic of support group, how closely a goal of the user (e.g., a wellness goal, such as a weight loss goal) matches the goals of other user of the support group, how closely attributes or preferences of the user match the attributes and preferences of members of the group, and so on.

In various embodiment, group members may be selected to become facilitators of a support group or enter to training to become a facilitator of a support group, members who become facilitators may be selected to become a facilitator of one of their own support groups or other support groups (e.g., based on various criteria, such as a judgment of effectiveness by the members of the other support groups, participation levels, or other criteria, such as the criteria used to select a support group for a non-facilitator).

In various embodiments, support groups may be reorganized based on various criteria, such as the size of the group, the ratio of facilitators to group members, promotions of group members to facilitators, demotions of facilitators to group members, automatic or voluntary movements of group members between groups (e.g., based on fit), changing goals, preferences, or attributes of users, and so on.

The methods and the various embodiments disclosed herein may be implemented as a computer system having one or more modules (e.g., hardware modules or software modules). The methods and the various embodiments disclosed herein may be embodied as instructions stored on a machine-readable medium that, when executed by a processor, cause the processor to perform the methods.

Figure 1:
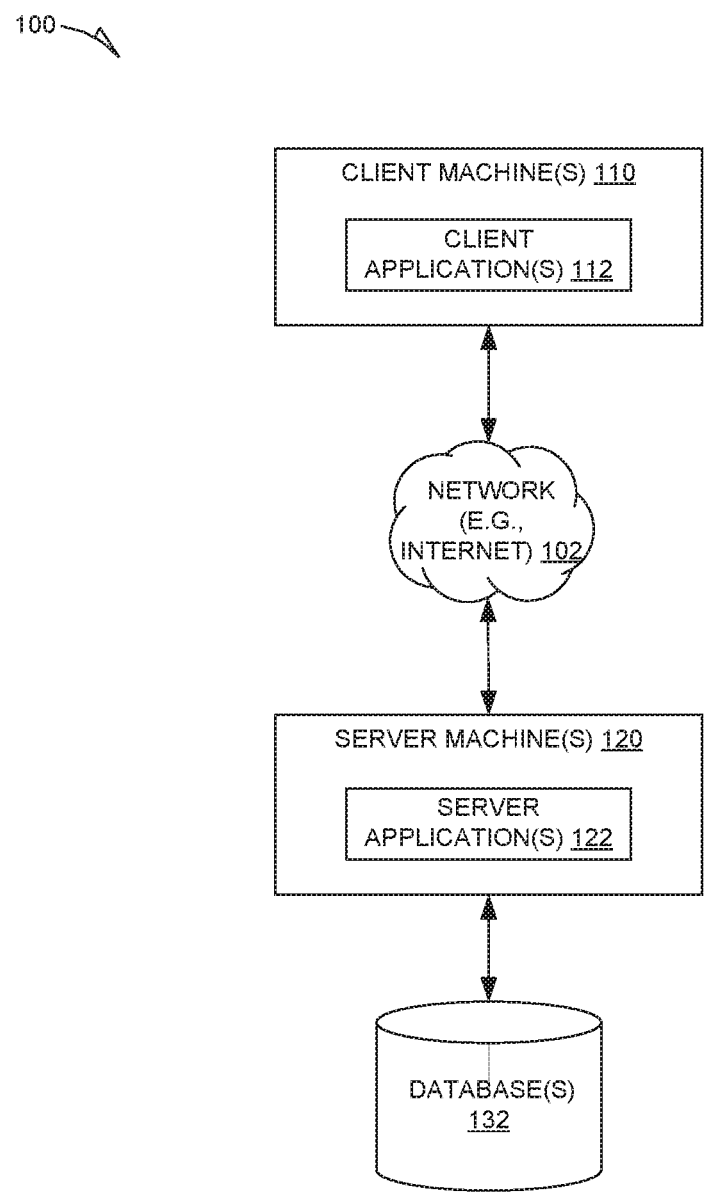
FIG. 1 is a network diagram depicting a client-server system within which various example embodiments may be deployed.

FIG. 1 is a network diagram depicting a system 100, within which various example embodiments may be deployed. The system 100 includes server machine(s) 120. Server application(s) 122 may provide server-side functionality (e.g., via a network 102) to one or more client application(s) 112 executing on one or more client machine(s) 110. Examples of client machine(s) 110 may include mobile devices, including wearable computing devices. A mobile device may be any device that is capable of being carried around. Examples of mobile devices include a laptop computer, a tablet computer (e.g., an iPad), a mobile or smart phone (e.g., an iPhone), and so on. A wearable computing device may be any computing device that may be worn. Examples of wearable computing devices include a smartwatch (e.g., a Pebble E-Paper Watch), an augmented reality head-mounted display (e.g., Google Glass), and so on. Such devices may use natural language recognition to support hands-free operation by a user.

In various embodiments, the client application(s) may include a web browser (e.g., a browser, such as the Internet Explorer browser developed by Microsoft Corporation of Redmond, Wash.), a native application (e.g., an application supported by an operating system of the device, such as Android, Windows, or iOS), or other application. Each of the one or more clients may include a module (e.g., a plug-in, add-in, or macro) that adds a specific service or feature to a larger system. In various embodiments, the network 102 includes one or more of the Internet, a Wide Area Network (WAN), or a Local Area. Network (LAN).

The server applications 122 may include an API server or a web server configured to provide programmatic and web interfaces, respectively, to one or more application servers. The application servers may host the one or more server application(s) 122. The application server may, in turn, be coupled to one or more data services and/or databases servers that facilitate access to one or more databases or NoSQL or non-relational data stores. Such databases or data stores may include database(s) 130 In various embodiments, the database(s) 130 include information provided by users of the wellness system information otherwise determined about users of the wellness system.

Such information may include information about meals users have eaten (e.g., based on logging of the meals by the users), unstructured interactions of the users with other users (e.g., in a support-group context), structured interactions of the users with other users (e.g., how many "high fives" a person has given or received), how consistently users have engaged in good habit-forming behaviors (e.g., how many meals in a row users have logged or how many meals users have logged today), attributes of the users (e.g., gender, age, height, weight, and so on), goals of the user (e.g., weight loss goals based on a starting weight and a target weight), preferences of the users (e.g., types of support groups the users are interested in joining or whether the users are interested in becoming facilitators of support groups), contact information (e.g., email addresses, home addresses, phone numbers, and so on), information users wish to share with other users, and so on.

The server application(s) 122 may provide a number of functions and services to users who access the sever machine(s) 120. While the server application(s) 122 are shown in FIG. 1 to be included on the server machine(s) 120, in alternative embodiments, the server application(s) 210 may form part of a service that is separate and distinct from the server machine(s) 120.

Further, while the system 100 shown in FIG. 1 employs a client-server architecture, various embodiments are, of course, not limited to such an architecture, and could equally well find application in a distributed, or peer-to-peer, architecture system, for example. The various applications could also be implemented as standalone software programs, which do not necessarily have computer networking capabilities. Additionally, although not shown in FIG. 1, it will be readily apparent to one skilled in the art that client machine(s) 110 and server machine(s) 120 may be coupled to multiple additional networked systems.

Figure 2A:
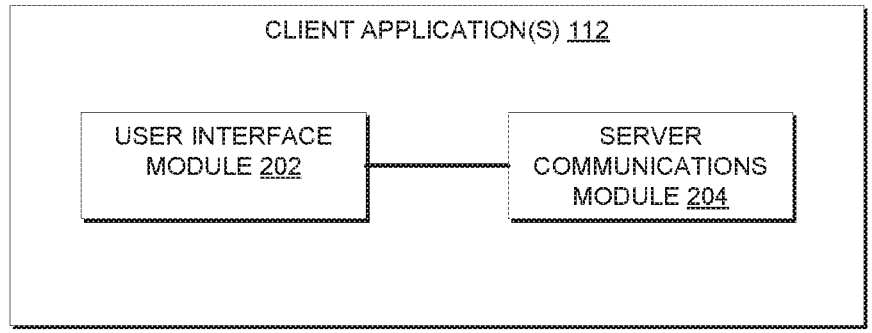
FIG. 2A is a block diagram illustrating example modules of the client application(s) 112.

FIG. 2A is a block diagram illustrating example modules of the client application(s) 112. A user interface module 202 may be configured to present a user interface pertaining to the server application(s) 122 on a client machine of the user, such as a mobile device. For example, the user interface module 202 may be configured to present any of the user interface screens depicted in FIGS. 7-18. A server communications module 204 may be configured to send communications to and receive communications from the server application(s) 122.

Figure 2B:
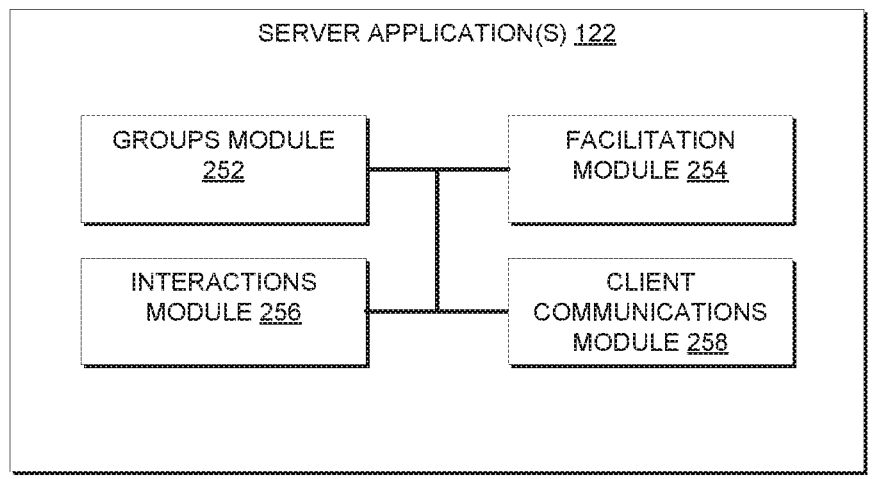
FIG. 2B is a block diagram illustrating example modules of the server application(s) 122 of FIG. 1. A groups module 252 may be configured to manage online support groups, including the creation, reorganization, or removal of support groups.

FIG. 2B is a block diagram illustrating example modules of the server application(s) 122 of FIG. 1. A groups module 252 may be configured to manage online support groups, including the creation, reorganization, or removal of support groups.

A facilitation module 254 may be configured to manage facilitation of the online support groups, including the nomination of group members to serve as facilitators or receive training as facilitators, the providing of such training, the promotion of group members to facilitators, the demotion of facilitators to group members, democratic elections of facilitators by group members, selection of qualified facilitators for particular groups, including groups other than groups to which the facilitator belongs, and so on.

An interactions module 256 may be configured to manage interactions between users of the wellness system, including structured interactions or unstructured interactions within a support group context, as described in more detail below. Furthermore, the interactions module 256 may be configured to support anonymous interactions between group members (e.g., allowing members of a support group to communicate while allowing the members to preserve their anonymity (e.g., like alcoholics anonymous)).

A client communications module 258 may be configured to send communications to or receive communications from the client application(s) 112.

Figure 3:
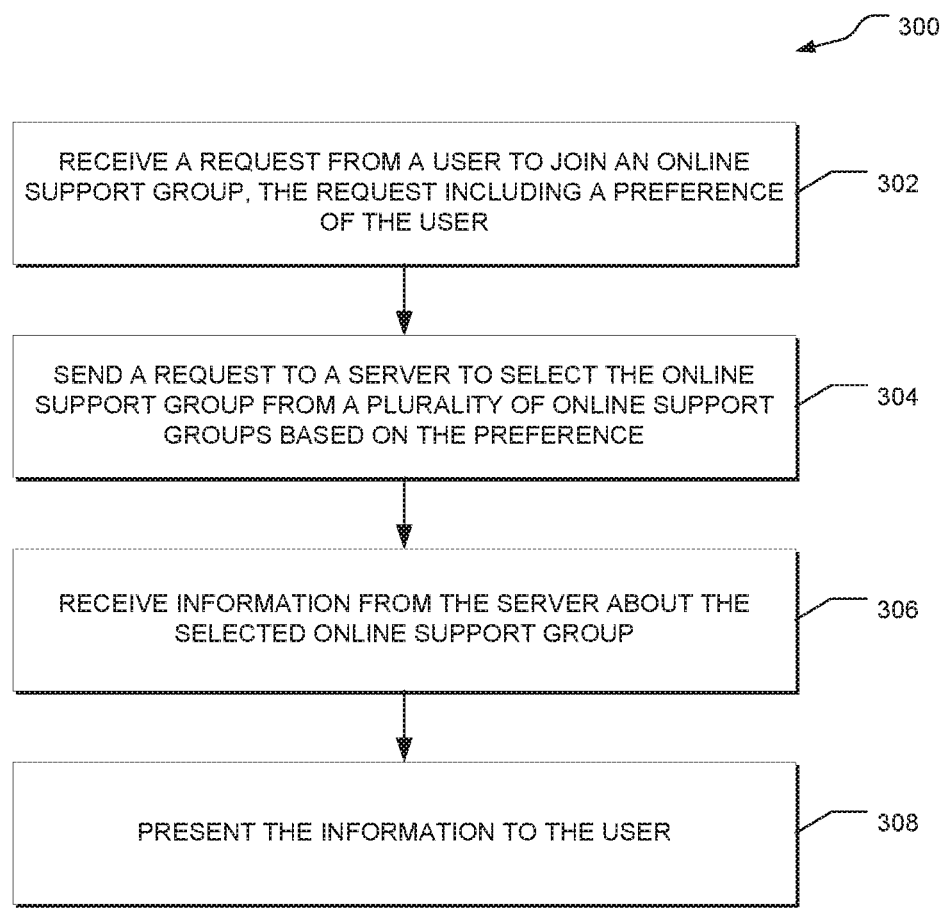
FIG. 3 is a flow chart illustrating example operations of a method 300 of allowing a user to join an online support group.

FIG. 3 is a flow chart illustrating example operations of a method 300 of allowing a user to join an online support group. In various embodiments, the method 300 may be implemented by one or more client application(s) 112. At operation 302, the user interface module 202 may receive a request from a user to join an online support group. For example, the user interface module 202 may detect that a user has clicked on a user interface element (e.g., the "Get Started!" button depicted in FIG. 10). In various embodiments, the request may include one or more preferences of the user with respect to a type of online support group the user would like to join. For example, the request may indicate that the user would like to join an online support group having members that are similar to the user in terms of one or more of the user's age, location, gender, weight goal, or other preferences. For example, the request may be generated based on input received from the user (e.g., via the user interface depicted in FIG. 12). In various embodiments, the request may indicate that the user does not have particular preferences or that the user wants to "get lucky" with respect to which online support group is selected for the user. In various embodiments, the user may not be provided with options for specifying which groups the user would prefer to join; instead, the group may be selected for the user automatically based on various factors described herein (e.g., the user's behavior within the client application(s), information provided by the user in a user profile, and so on).

At operation 304, the server communications module 204 may send one or more communications to the server application(s) 122. For example, the server communications module 204 may send the request, an identification of the user sending the request, and the preferences of the user with respect to the request.

At operation 306, the server communications module 204 may receive a response to the request from the server application(s) 122. The response may include information about an online support group that was selected for the user. In various embodiments, the online support group may be selected for the user based on information received from the user or determined about the user, the information in the request, and the information about the user preferences, as will be described in more detail below.

At operation 308, the user interface module 202 may present at least a subset of the information about the selected online support group to the user. For example, the user may be provided with information about the group, including current members of the group. The information about members of the group may include profile data submitted by the members of the group. The profile data may include photos, introductions, or other data shared by the users about themselves. In various embodiments, the information may include information about goals of each member and progress of each member toward reaching those goals, as will be described in more detail below. In various embodiments, the actual identities of the users may not be disclosed, such that the support group may operate as an anonymous support group. Alternatively, identities of the members of the support group may be disclosed to other members.

Figure 18:
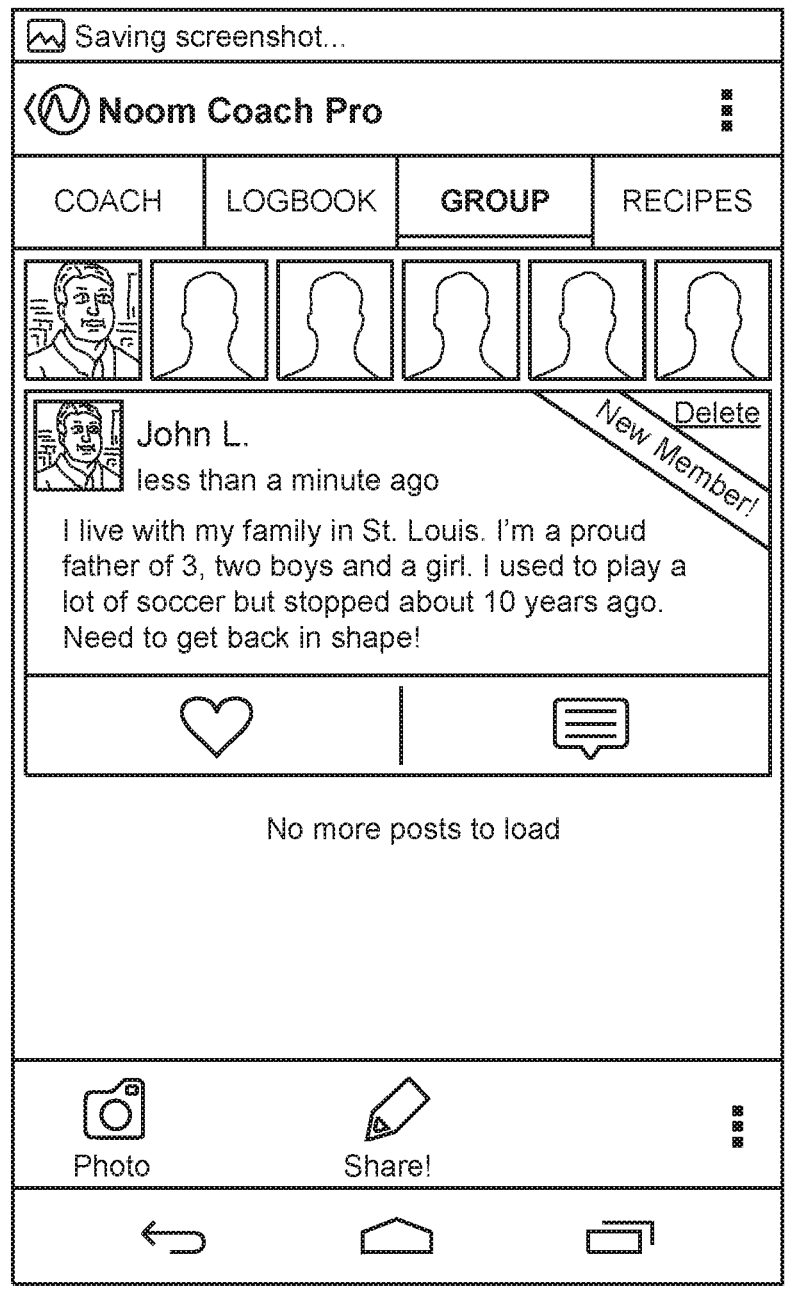

In various embodiments, whether the support group is anonymous or not may be controlled by a configuration option. In various embodiments, the configuration option may be set by an administrator or by a facilitator of the group. In various embodiments, whether a support group is anonymous or not may be a criterion upon which a selection of a group for a user is based. In other words, the user may be able specify whether he wishes to join an anonymous support group or not, and an online support group may then be selected for the user based on the user's specification. An example user interface in which information about the group may be presented to the user is depicted in FIG. 18.

In various embodiments, the user interface module 202 may further present the user with an option to join the group. In various embodiments, the user may be provided with options to complete the join flow again to join a different group or one or more additional groups.

Figure 4:
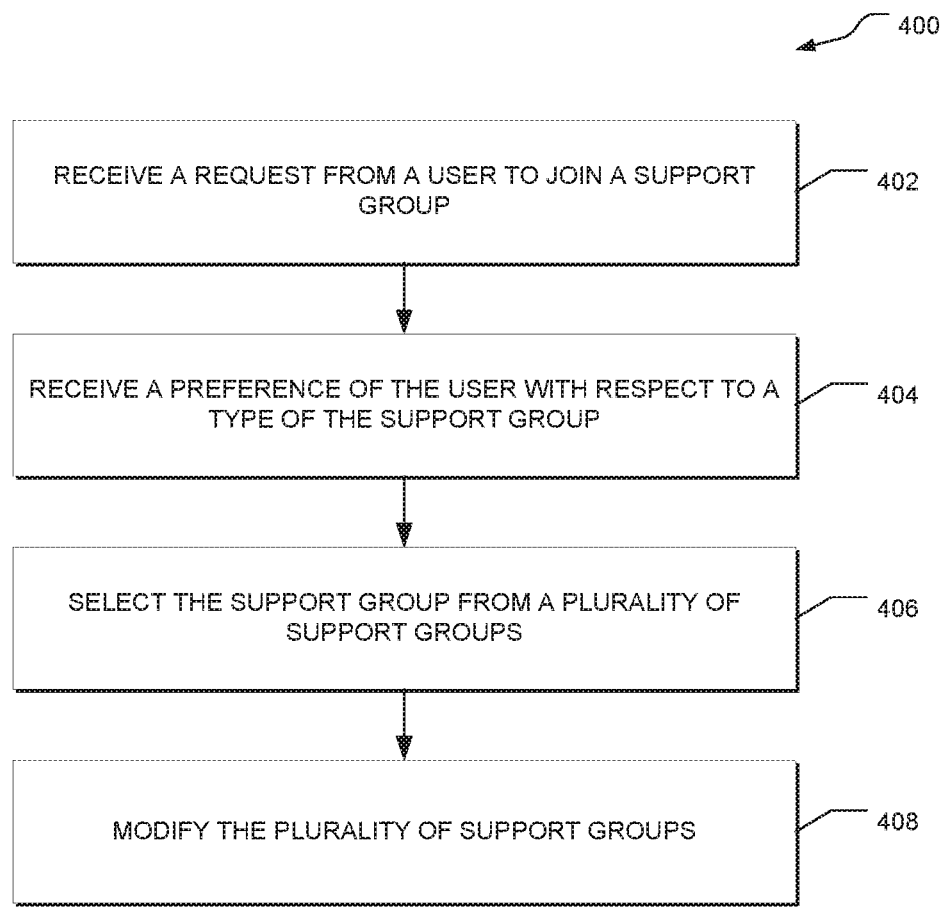
FIG. 4 is a flow chart illustrating example operations of a method 400 of processing a request from a user to join an online support group.

FIG. 4 is a flow chart illustrating example operations of a method 400 of processing a request from a user to join an online support group. In various embodiments, the method 400 may be implemented by one or more server application(s) 122.

At operation 402, the client communications module 258 may receive a request from a user to join a support group.

At operation 404, the client communications module 258 may receive information pertaining to the request, such as an identification of the user, a preference of the user, and so on. For example, the information may include a specification that the user would like to join an online support group having members that are similar to the user in terms of one or more of the user's age, location, gender, weight goal, or other preferences. In various embodiments, such additional information may be included in the request received at operation 402.

At operation 406, the groups module 252 may select a support group for the user. In various embodiments, the groups module 252 may base the selection on information about the user that was provided by the user (e.g., in public posting by the user, in profile data provided by the user, and so on) or information about the user that was determined by the wellness system (e.g., based on search data, user behavior data, and so on). In various embodiments, the groups module 252 may base the selection on similarities between information about the user and information about others users of the set of existing groups, such as similarities in age, height, weight, location, genders, goals (e.g., a target weight goal), progress toward goals (e.g., a percentage of progress to a target weight already achieved based on starting weight), group participation levels, and so on. In various embodiments, the groups module 252 may base the selection on preferences of the user with respect to similarities that are important to the user or on preferences of the current members of the existing groups with respect to such similarities.

At operation 408, the groups module 252 may modify a current set of support groups. For example, the groups module 252 may create a new group. Or the groups module 252 may move a current member of an existing group to a different group. Or the groups module 252 may remove a group and move all of its current members to different groups. In various embodiments, the groups module 252 may modify the groups based on an acceptance of an invitation to the user to join a selected group. For example, based on the joining of the user to an existing group causing a size of the group to exceed a size threshold, the groups module 252 may separate the group into two different groups. Or based on a moving of a member of an existing group to a new group causing the size of the existing group to fall below a size threshold. The groups module 252 may remove the group and move the remaining members to different groups.

In various embodiments, the groups module 252 modifies the support groups to accommodate changes in user attributes, preferences, or group dynamics. Thus, as new users join support groups or existing users move between support groups, change goals, become more or less active within the wellness system, and so on, the groups module 252 optimizes the groups to bring users together based on various optimization criteria, including similarities, preferences, and participation levels. The success of the optimization may be based on various measurement criteria, such user satisfaction with group dynamics, participation levels of group members, rates of success of users at achieving their goals, and so on. Thus, supports groups may be modified dynamically as new information is received or collected by the wellness system.

In various embodiments, the groups module 252 manages a persistence layer that stores individual member information, individual group information, and information about which groups a particular member belongs to and in which roles. This persistence layer may be implemented using a commercial SQL or no-SQL database to guarantee the ACID nature of storage.

In various embodiments, the groups module 252 includes a caching layer that contains selected information from the persistence layer, but laid out in a way that facilitates the dynamic group clustering/search process. For example, the information about which members belong to which groups, key stats about group activity, and individual member activity are stored in memory to facilitate fast queries. Because there can be millions of members, across hundreds of thousands of groups, and clustering must be done quickly and frequently, such a caching layer can significantly boost system performance.

In various embodiments, merging of groups and other group modifications may be performed invisibly to the user, based on weighted implicit and explicit variables. Members may be automatically moved into new groups or clusters based on recalculation or reweighting of variables, including performance of the current group clustering.

Merging may be guided by explicit variables, provided by the user in response to a prompt, throughout the use of the application or at the time of joining, including age, gender, body-mass index (BUD, weight loss goal, time zone, and/or life characteristics like, is the person married, dating, or single, their sexual orientation, number of children, religious affiliation, daily schedule, usage of different types of transportation, dietary preferences (e.g. vegetarian, vegan, etc.), exercise habits, exercise preferences, body-mass index (BMI) history, or keywords that the user provides when searching for a group.

Merging may also be guided by implicit variables (e.g., data gathered by monitoring user activity), for example, activity level within the app (e.g. number of sessions per month/week/day, minutes per session, actions per session), physical activity level (e.g. steps per day, exercises logged per time period), types of physical activity (e.g. those who log certain types of exercise), types of foods logged, healthiness of food eaten, or logging habits (e.g. frequency of logging. Other attributes that may be considered include the user's location, time zone, operating system of client device, and so on.

Merging may be attended by communication with all or a subset of affected users and facilitators, potentially asking for permission to re-structure the group, with or without explanation as to why the experience will be improved by the merging operation.

Figure 5:
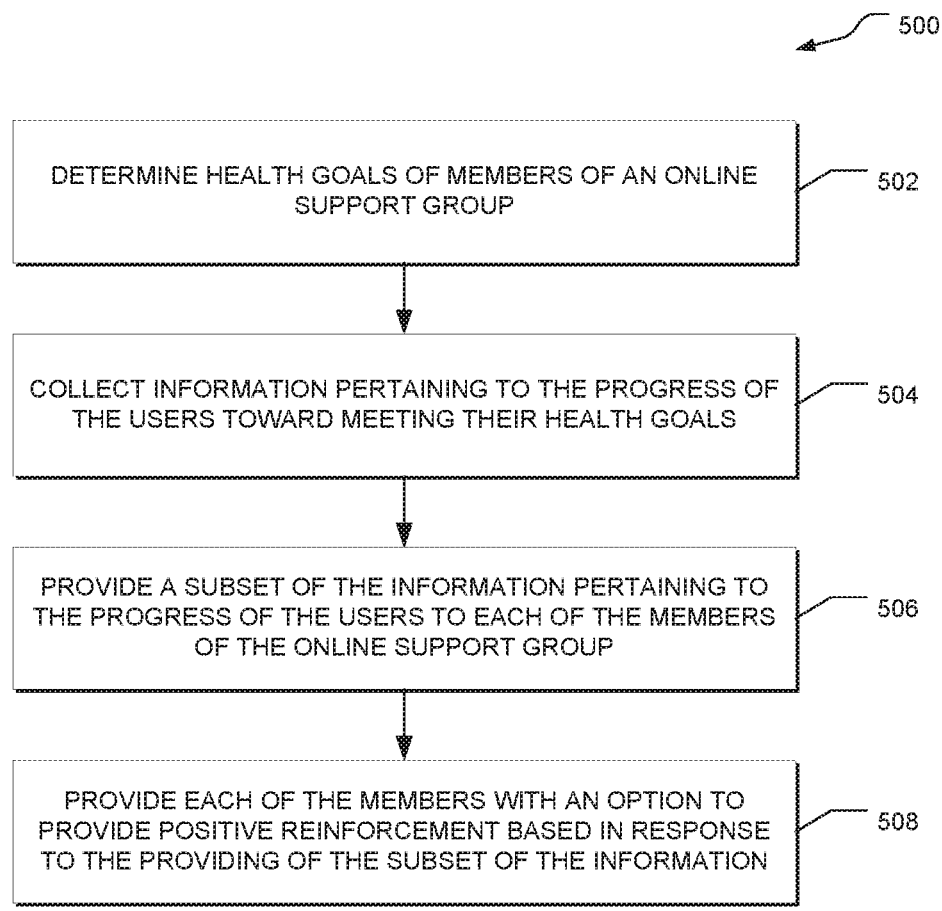
FIG. 5 is a flow chart illustrating example operations of a method 500 of fostering positive interactions between members of an online support group.

FIG. 5 is a flow chart illustrating example operations of a method 500 of fostering positive interactions between members of an online support group. In various embodiments, the method 500 may be implemented by one or more server application(s) 122. At operation 502, the groups module 252 may determine health goals of members of an online support group. For example, the groups module 252 may determine that a user wishes to attain a particular goal weight. Or the groups module 252 may determine that a user wishes to attain a particular fitness level. Or the groups module 252 may determine that the user has a particular dietary goal.

At operation 504, the groups module 252 collects information pertaining to the progress of the users toward meeting their health goals. For example, the groups module 252 may determine that the user has made a particular amount of progress toward reaching a target weight based on a starting weight. Or the groups module 252 may determine that the user has logged a certain number of meals in a row. Or the groups module 252 may determine that the user has logged a certain number of meals today. Or the groups module 252 may determine that the user has accomplished a sub-goal (e.g., performed a task, such as walking for 30 minutes, lifting weights, and so on, on a number of consecutive days.

At operation 506, the groups module selects a subset of the information pertaining to the progress of the user to each of the other members of the user's online support group. For example, the groups module 252 selects particular sub-goals for which the user would likely most benefit from encouragement from the group. The groups module 252 may select the particular sub-goals based on various selection criteria, such as a consistency with which the user has achieved the sub-goal in the past.

Figure 9:
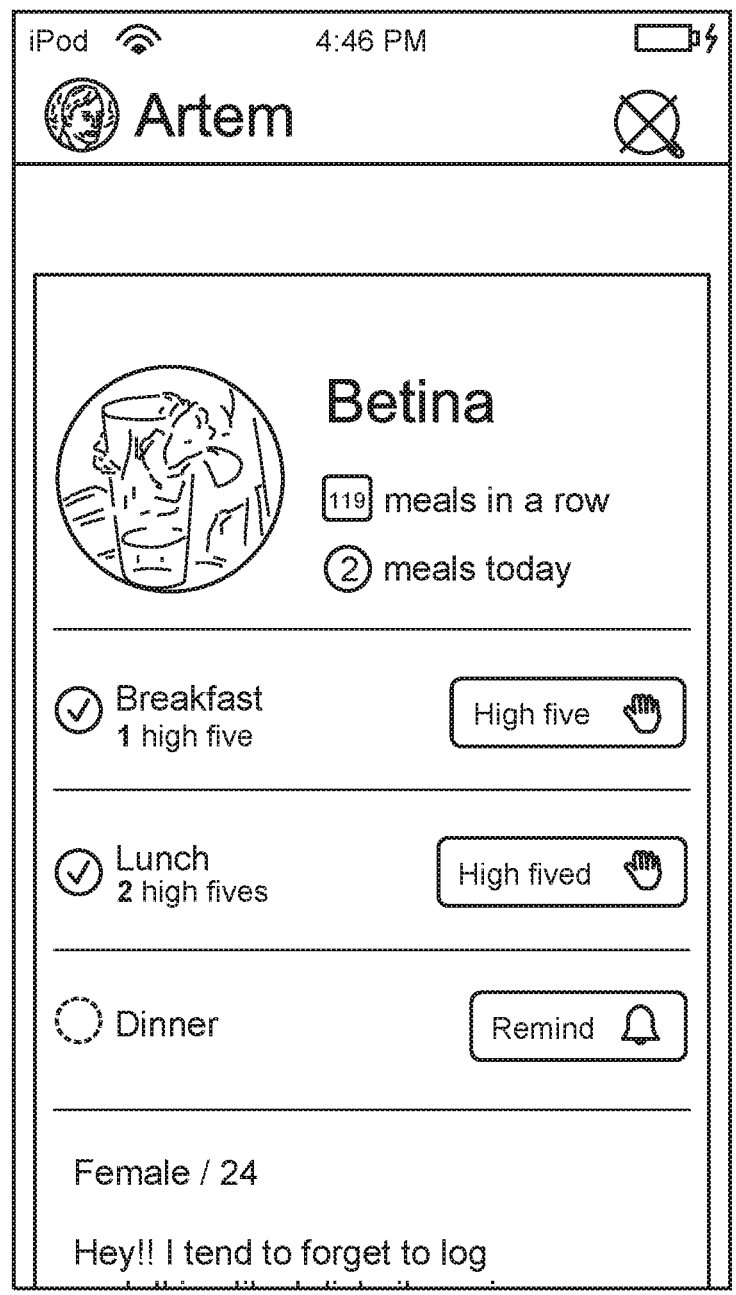

At operation 508, the interactions module 256 may provide each of the members with an option to provide positive reinforcement to the user based on the selected subset of the information pertaining to the progress of the user. For example, the interactions module 256 may generate a content page that is to be presented to each of the members of the group that includes an option for each of the members of the group to provide positive reinforcement (e.g., a "high five" as depicted in FIG. 9. The interaction module 256 may then communicate this content page (e.g., via the client communications module 258) to the client application(s) 112 (e.g., for presenting to the user on a mobile device of the user). Furthermore, the interactions module 256 may communicate to the user any such positive reinforcement received from the members of the user's group. The receiving of positive reinforcement from the support group may help motivate the user to accomplish a goal or sub-goal.

Figure 12:

In various embodiments, the interactions module 256 provides group members with opportunities for unstructured, semi-structured, and structured interactions with other group members. Examples of semi-structured group interactions may include invitations for new members to introduce themselves by answering questions (e.g., as curated by a human, such as a group facilitator), options to invite specific members (e.g., friends or family members) to join the group, and so on. Examples of unstructured group actions may include options to share information in unstructured form (e.g., as depicted in FIG. 12). In various embodiments, users can share freeform text comments. Other users can comment or like these and other types of posts. Users can be prompted to post success stories, in different forms (e.g. text, photos, drawings, sound, static graphic art, moving graphic art, video, annotated media, etc.).

Examples of structured data may include showing of a member's count of continuously logged meals. The count may be displayed in conjunction with profile data of the user (e.g., a username of the user). Group members may be provided with an option to high-five or comment on that streak. The system may further highlight the content of meals or average healthfulness of meals that this person is consuming, progress toward goals, and so on. Group members can see each other's progress, where progress indicators are designed to form good habits. Such progress indicators reward continuous task performance, such as meal logging. In various embodiments, most or all progress may be lost when the continuity is interrupted (e.g., when one meal is not logged). In various embodiments, points for each individual pattern/behavior/sub-goal are kept separately instead of unified into a single point system. In this way, certain negative aspects associated with a points system, such as introducing certain psychological issues of making the reward seem less intrinsic in the activity, may be reduced or avoided. Thus progress indicators may refer to separate tracking of each type of pattern/behavior.

In various embodiments, at least some of the data within the feed can be drawn from structured data (e.g., to simplify use within automated tools for optimizing group behavior). For example, individual activities (e.g. logging of a specific meal, number of meals or exercised logged, or types of foods logged) can be automatically shared, or users can be invited to share these. For another example, weekly summaries of different activity types, visually inviting, can be automatically prepared for automatic or explicit sharing.

In various embodiments, the system tracks and positively reinforces behaviors that lead to effective habit formation. Examples include continuously logging 3 meals every day without skipping a single one (zero tolerance for skipping), a minimum amount of exercising daily, continuous weekly weigh-ins, continuous achievement of daily goal(s) which reset to zero or are otherwise reduced when pattern is broken.

In various embodiments, the system also reinforces behaviors that directly contribute to meeting wellness goals. Examples include progress indicators increase for meeting certain healthfulness of meals (e.g. 3 healthy meals in 5 days), or progress indicators for consumption of certain foods (e.g. 2 soups today!).

In various embodiments, the system further reinforces group dynamics by rewarding group cooperation. For example, groups can be rewarded when everyone in the group logs a certain meal or all of their meals for the day. For another example, groups can be rewarded when a group achieves 95% participation and an aggregate total step goal of 100,000 steps.

In various embodiments, the system may further reinforce group dynamics by making virtual groups engage in friendly competition with each other by exposing target metrics (e.g. total meals logged in a group) to other groups and showing a global/local ranking of groups based on these metrics.

In various embodiments, the member feedback mechanism may likewise emphasize positive feedback from group members and deemphasize negative feedback from group members. This serves as mostly positive reinforcement (peer pressure) to assist the user in reaching a goal.

In various embodiments, periodicity, cadence, and challenge level of sub-goals may be optimally selected to be habit forming and the reward may be based on ability of the user to achieve sub-goals at the selected cadence. The optimal cadence for fast habit formation for a behavior may be the same behavior whenever a certain stimulus is presented, with an intrinsic variable reward immediately following the target behavior. For example, logging every major meal (breakfast, lunch, dinner) right after completion of that meal, and receiving a variable number of high-fives from the group shortly after doing so. Cadence is therefore chosen based on the frequency of a potential stimulus in the environment.

In various embodiments, beyond cadence, each step of the habit itself may become more challenging, e.g. the user is challenged to take a photo at each meal they log. Cadence and challenge level are adjusted to allow marginal user contribution to achieve a marginal success at completing the goal. Group members can see each other's failures (e.g., missed logging of a meal, missed exercise, etc.).

Figure 6:
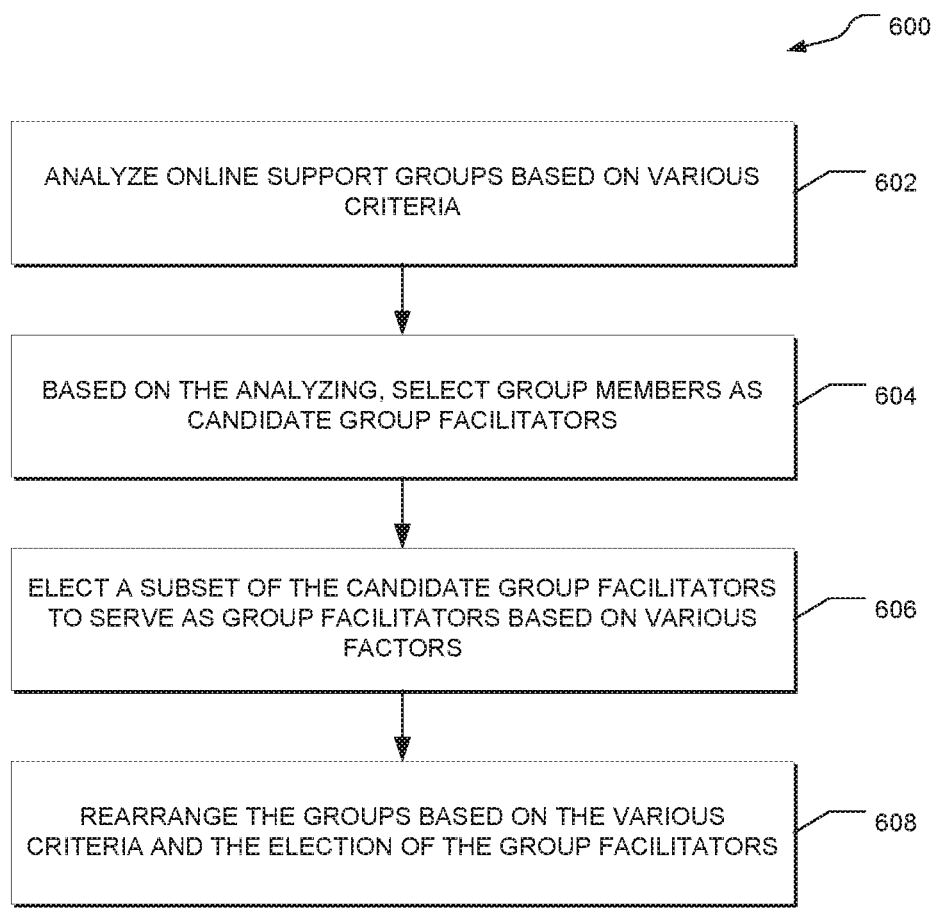
FIG. 6 is a flow chart illustrating example operations of a method 600 of using facilitation to enhance a dynamic of an online support group.

FIG. 6 is a flow chart illustrating example operations of a method 600 of using facilitation to enhance a dynamic of an online support group. In various embodiments, the method 500 may be implemented by one or more server application(s) 122. At operation 602, groups module 252 analyzes a set of existing support groups based on various criteria, such as participation levels of group members, satisfaction scores of group members, rates of success of users in attaining their goals, an experience level of the facilitator of the group, user satisfaction with the facilitator of the group, and so on.

At operation 604, the facilitation module 254 selects a subset members of the group as candidates to serve as group facilitators of their current group or of another group. For example, the facilitation module 254 may select a user as a candidate to serve as a group facilitator based on the participation level of the user being a measure higher than other members of the group. Or the facilitation module 254 may select the user based on the user having a higher success rate at attaining goals than the other users. Or the facilitation module 254 may select the user based on a level of experience of the user with the system.

At operation 606, the facilitation module 254 allows members of the group to democratically elect one or more facilitator nominees. The nominees may include the current facilitator of the group and the one or more group members selected at operation 604.

At operation 608, the facilitation module 254 rearranges the groups based on the election of the group facilitators. For example, if a democratically-elected facilitator replaces an incumbent facilitator, the incumbent facilitator may be provided with an option to become a facilitator of another group. Or, based on the votes suggesting a strong popularity of multiple nominated members to serve as facilitator, one or more of the multiple group members may be provided with an option to become a facilitator of different group. In various embodiments, the different group may be selected for the facilitator based on the different group lacking a strong facilitator (e.g., based on success rates of group members attaining their goals or other criteria) or any of the criteria used to select a group for a new member.

In various embodiments, the facilitation module 254 may provide selected group members with an option to receive training pertaining to group facilitation. The facilitation module 254 may then provide training instructions and rate the competency of the candidate group member to server as a facilitator. In various embodiments, group members may be promoted to serve as facilitators and facilitators may be demoted from facilitators to group members based on any combination of training, experience, popularity, or other factors.

In various embodiments, the facilitator administers the group and bears additional responsibility for group success. Having such a person avoids the division of responsibility that may result without a facilitator. Furthermore, having facilitators of various skill levels and in training may increase the supply of facilitators, thus decreasing their cost.

The members may have the ability to vote for a facilitator or may be automatically selected by the system based on past performance and expressed preference for facilitation. The members can then choose to vote out the facilitator by majority, plurality or weighted voting. A new facilitator is in turn explicitly selected by group members or appointed by the system.

The facilitator may have special powers compared to other members of the group. These special powers may include kicking people out of the group, inviting people into the group, bestowing certain rewards for achievements by group members, broadcasting messages to all members of a group, and so forth. The facilitator may be able to access additional semi-private information about group members that is not visible to other group members, such as amount of weight lost by a member.

The facilitator may be responsible for ensuring the highest possible level of group participation, group members satisfaction, etc. The facilitator may carry out these responsibilities by participating actively in the group, posting content, or re-posting content automatically suggested to him or her by the system.

The system may provide additional training to the facilitator in the form of automatically delivered educational content (email, in-app or web-based), assisted by human coaching (e.g., as provided by employees of the company deploying the wellness system).

The system may further assist the facilitator though the server-side measures such as abusive or inactive member management.

The facilitation module 254 may enable administrative management of facilitators, whereby facilitators can be rewarded, reelected, moved, voted out, or selected for coaching. Facilitators may be rated based on group metrics, for example, participation level of members (average, minimum amount, frequency of participation, type and variety of participation), progress of members towards meeting their goals (weigh-ins completed, weight lost, meals logged, exercises logged), satisfaction of members (quantitative and qualitative, measured via surveys, interviews, or other means, about their experience with the wellness system, their group, and their facilitator, average happiness of members, a certain number of members above a minimum satisfaction threshold, or a limit on number of low satisfaction scores). Based on his or her rating, a facilitator may be selected to receive coaching, or could be rewarded for strong performance.

Figure 7:
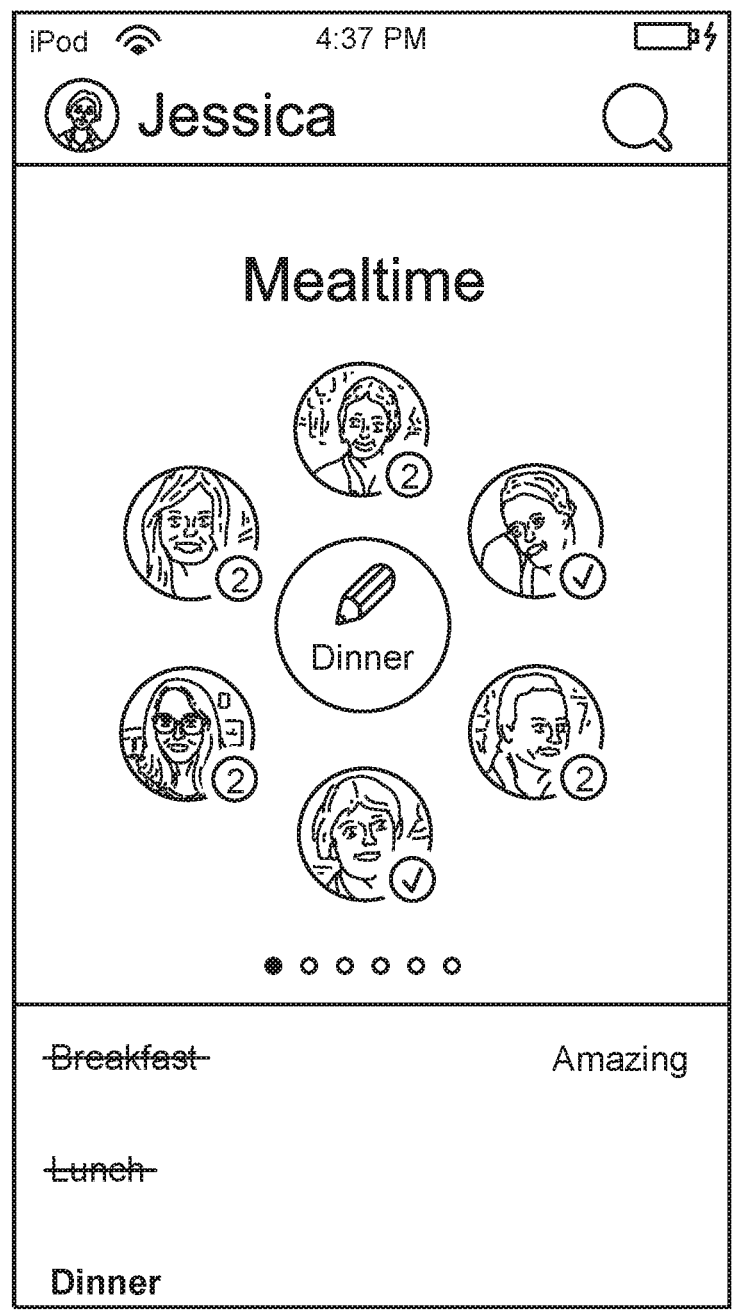

FIG. 7 is a screenshot of an example user interface for logging progress toward reaching sub-goals and viewing progress of other group members pertaining to the same sub-goal. In various embodiments, the user interface may be presented by the user interface module 202. As depicted in FIG. 7, the progress of each member of the online support group at reaching a sub-goal (e.g., logging a meal, such as dinner) may be presented in visual form. For example, photos of the members may be shown around a user interface element representing the sub-goal. Group members who have completed all sub-goals related to the sub-goal (e.g., logging breakfast, lunch, and dinner for the day) may have a check-mark placed next to their name. Those who have partially completed all of the sub-goals may have a number placed next to their name indicating how many of the related sub-goals each of the group members have completed (e.g., a "2" may represent that the group members have completed two of the related sub goals, such as logging breakfast and dinner). In various embodiments, the user interface is presented based on the time corresponding to an approximate time at which the goal is to be completed. Thus, the user interface depicted in FIG. 7 may be presented around dinner time, when it is expected that the group members are to complete their sub-goal of logging their dinner meal.

Figure 8:
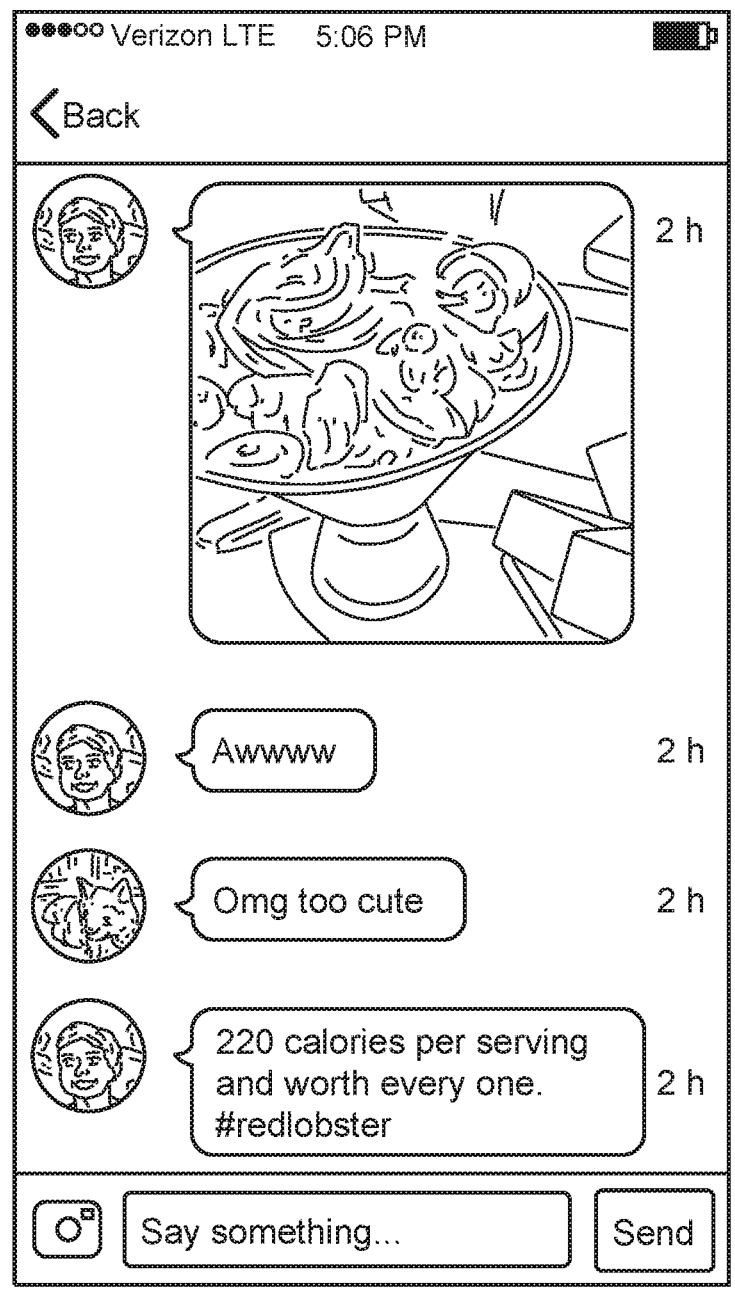

FIG. 8 is a screenshot of an example user interface for allowing unstructured communications between group members. In various embodiments, group members may share photos, such as a photo pertaining to a goal. For example, group members may share photos of meals that they will be logging later. In various embodiments, group members may be able to respond to postings by other group members.

FIG. 9 is a screenshot of an example user interface for allowing structured communications between group members. As depicted in FIG. 9, a group member may be able to view another group member's progress toward attaining a goal or sub-goal. For example, a group member may be able to view another group member's progress toward logging meals. The progress may indicate a number of meals in a row that the group member has logged as well as a number of meals that the group member has logged today. The viewing group member may be able to respond with positive feedback to the group member who has completed the sub-goal (e.g., by giving a "High Five"). Additionally, the viewing group member may be able to provide encouragement to the group member to complete a sub-goal that the group member has not completed (e.g., by triggering a reminder to the group member to complete the sub-goal). Additionally, the viewing group member may be able to submit a comment, such as a comment providing additional encouragement.

Figure 10:

FIG. 10 is a screenshot of an example user interface for joining an online support group. The user interface may provide a user with information pertaining to the online support groups, such as how they work. The user may then be able to click on a user interface element (e.g., a "Get Started!" button) to indicate that the user is interested in joining an online support group.

Figure 11:
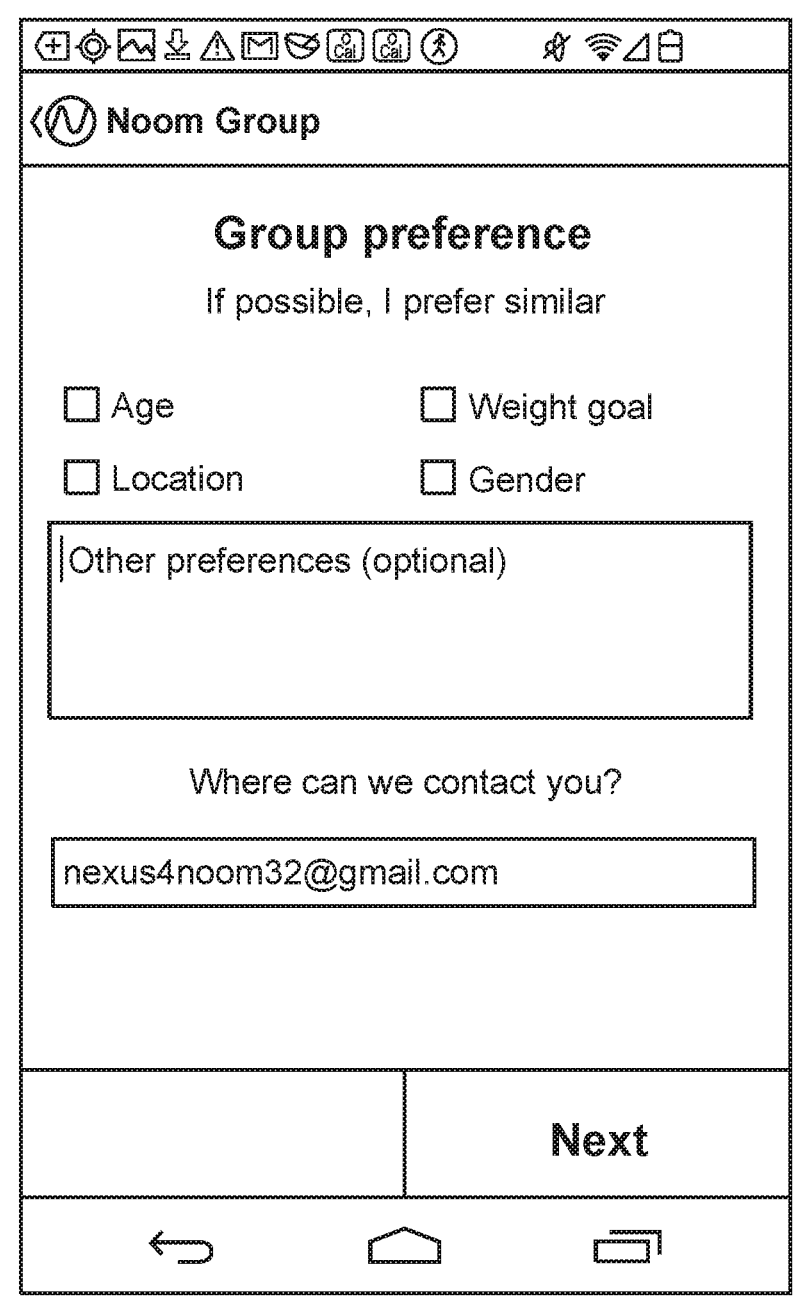

FIG. 11 is a screenshot of an example user interface for specifying group preferences. The user interface may allow the user to specify that the user wishes to join a group in which the group members have a similar age, location, weight goal, gender, or other similarities. Additionally, the user may be able to specify contact information (e.g., an email address).

FIG. 12 is a screenshot of the example user interface depicted in FIG. 11 with various fields filled in. Here, the user has specified that he would like to join a group in which the members of the group have a similar age, location, weight goal, and gender. Additionally, the user has specified that he is a new dad and is interested in joining a group with other new dads.

Figure 13:
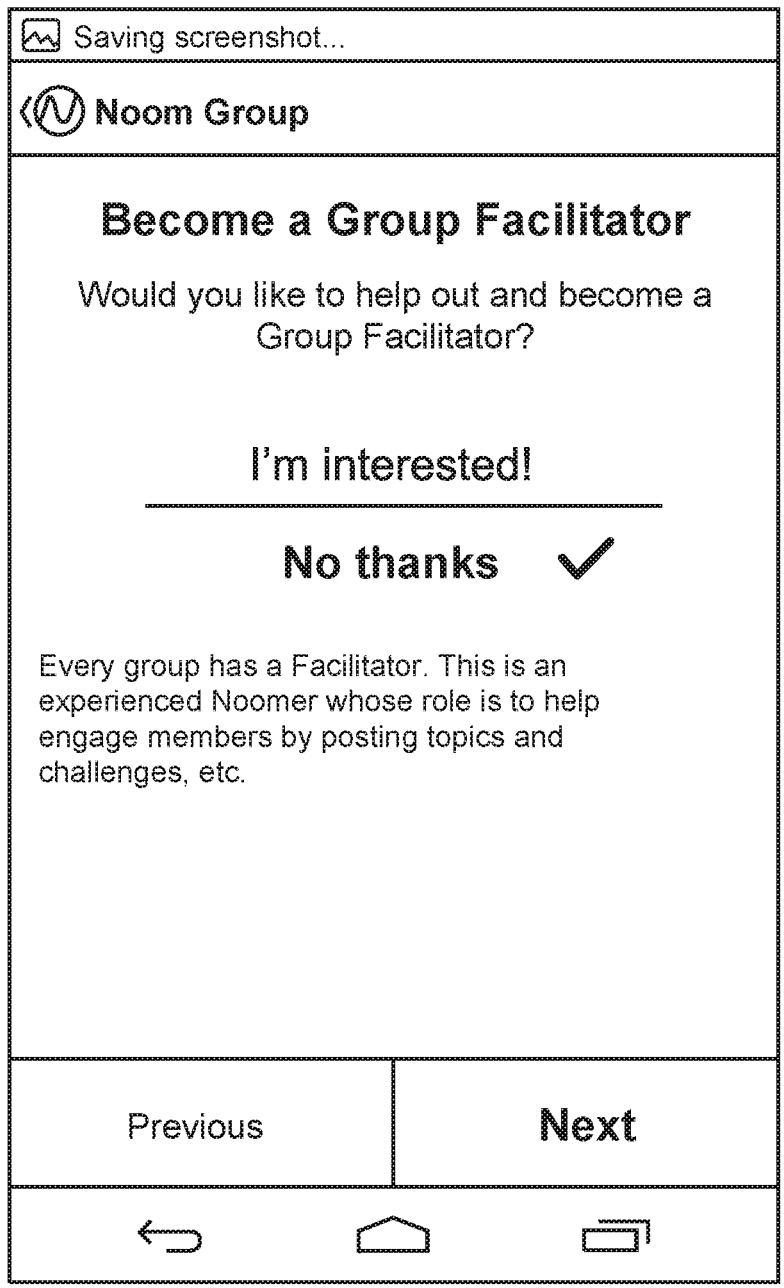

FIG. 13 is a screenshot of an example user interface that allows a user to specify whether he is interested in becoming a facilitator of a group.

Figure 14:
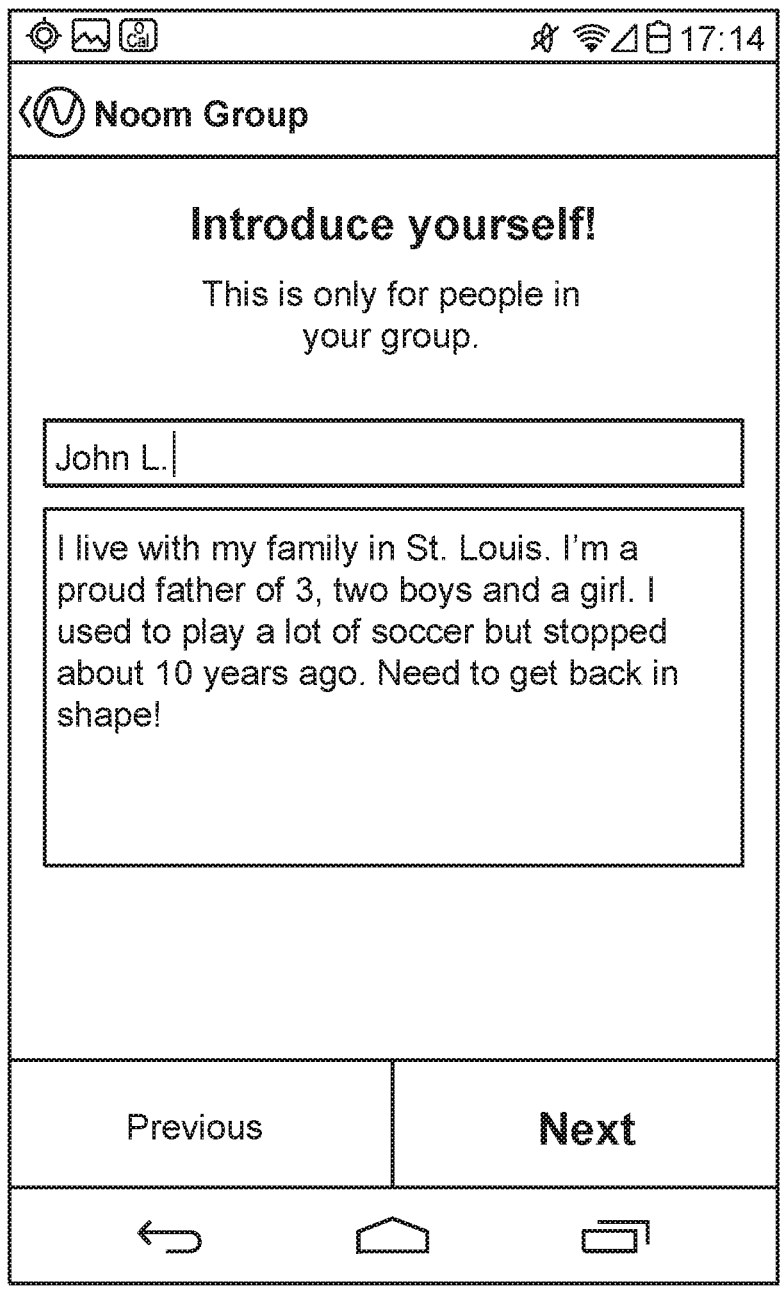

FIG. 14 is a screenshot of an example user interface that allows a new member of a group to introduce himself to other members of the group. In various embodiments, the information provided by the member is only shared with other members of the group.

Figure 15:
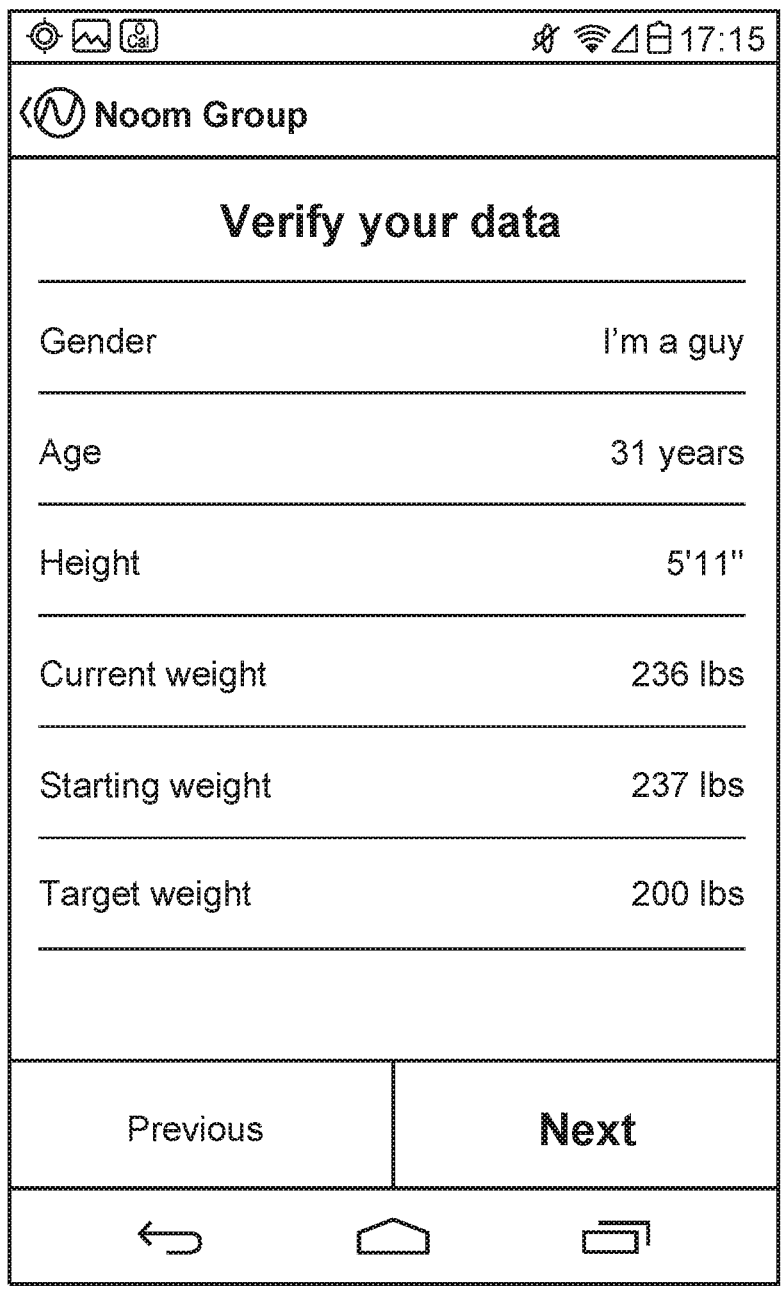

FIG. 15 is a screenshot of an example user interface that allows a user to verify data pertaining to the user, such as the gender, age, height, current weight, starting weight, and target weight of the user.

Figure 16:
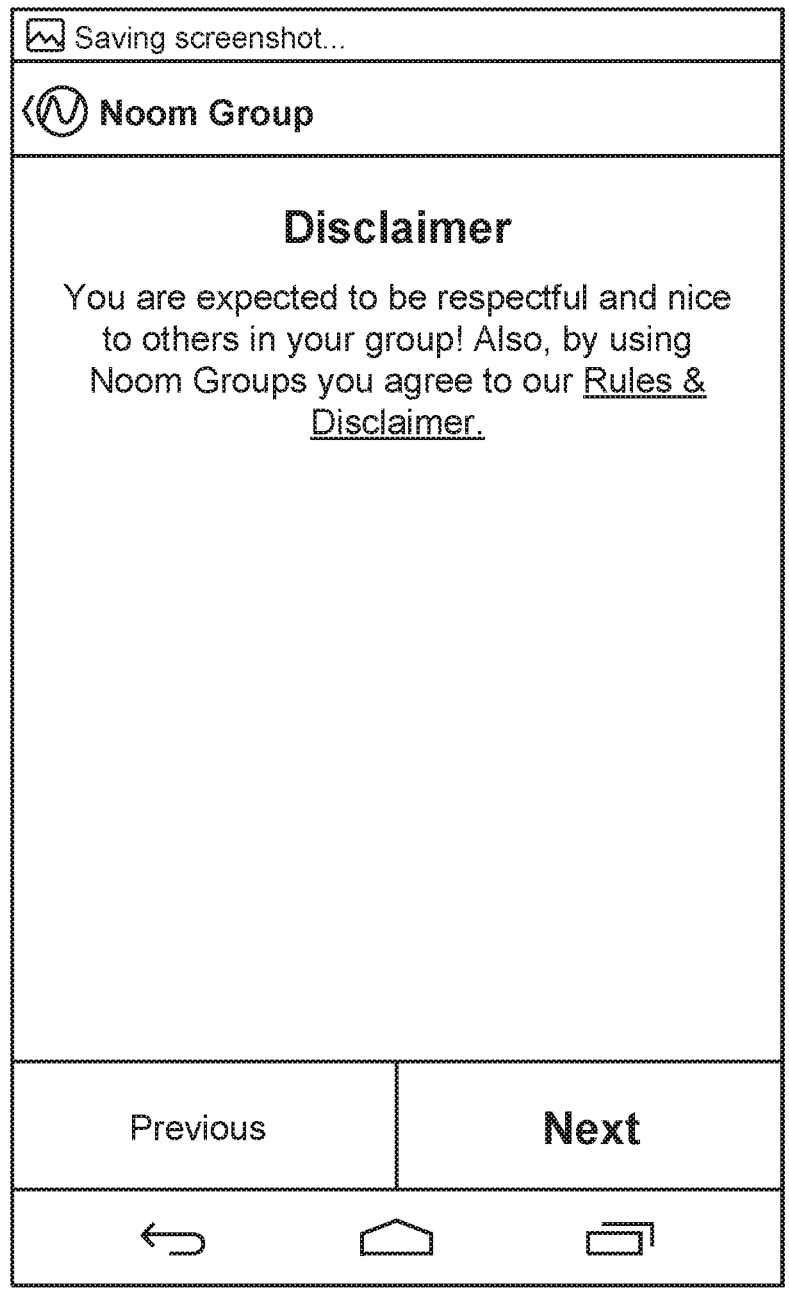

FIG. 16 is a screenshot, of an example user interface for providing a disclaimer to the user before the user joins the group.

Figure 17:
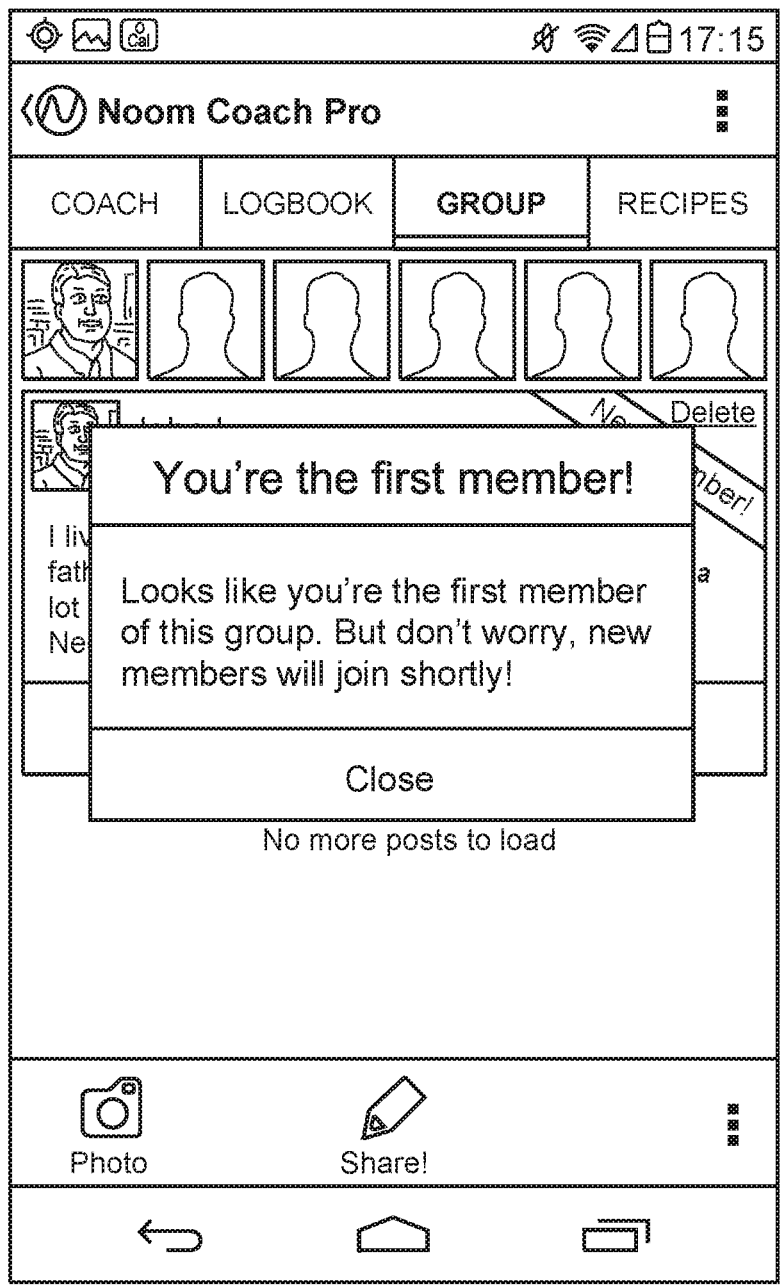

FIG. 17 is a screenshot of an example user interface for providing the user with information about a group that the user has been invited to join. In various embodiments, a new group may be created for a user. Eventually additional users will be selected to join the user's group.

FIG. 18 is a screenshot of an example user interface for providing the user with information about other members of the group. In various embodiments, the user may be able to select photos of other group members to view information about the other group members, such as their progress toward meeting their wellness goals.

Certain embodiments are described herein as including logic or a number of components, modules, or mechanisms. Modules may constitute either software modules (e.g., code embodied on a machine-readable medium or in a transmission signal) or hardware modules. A hardware module is a tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the network 120) and via one or more appropriate interfaces (e.g., APIs).

Example embodiments may be implemented in digital electronic circuitry, or in computer hardware, firmware, software, or in combinations of them. Example embodiments may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry (e.g., a FPGA or an ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Figure 19:
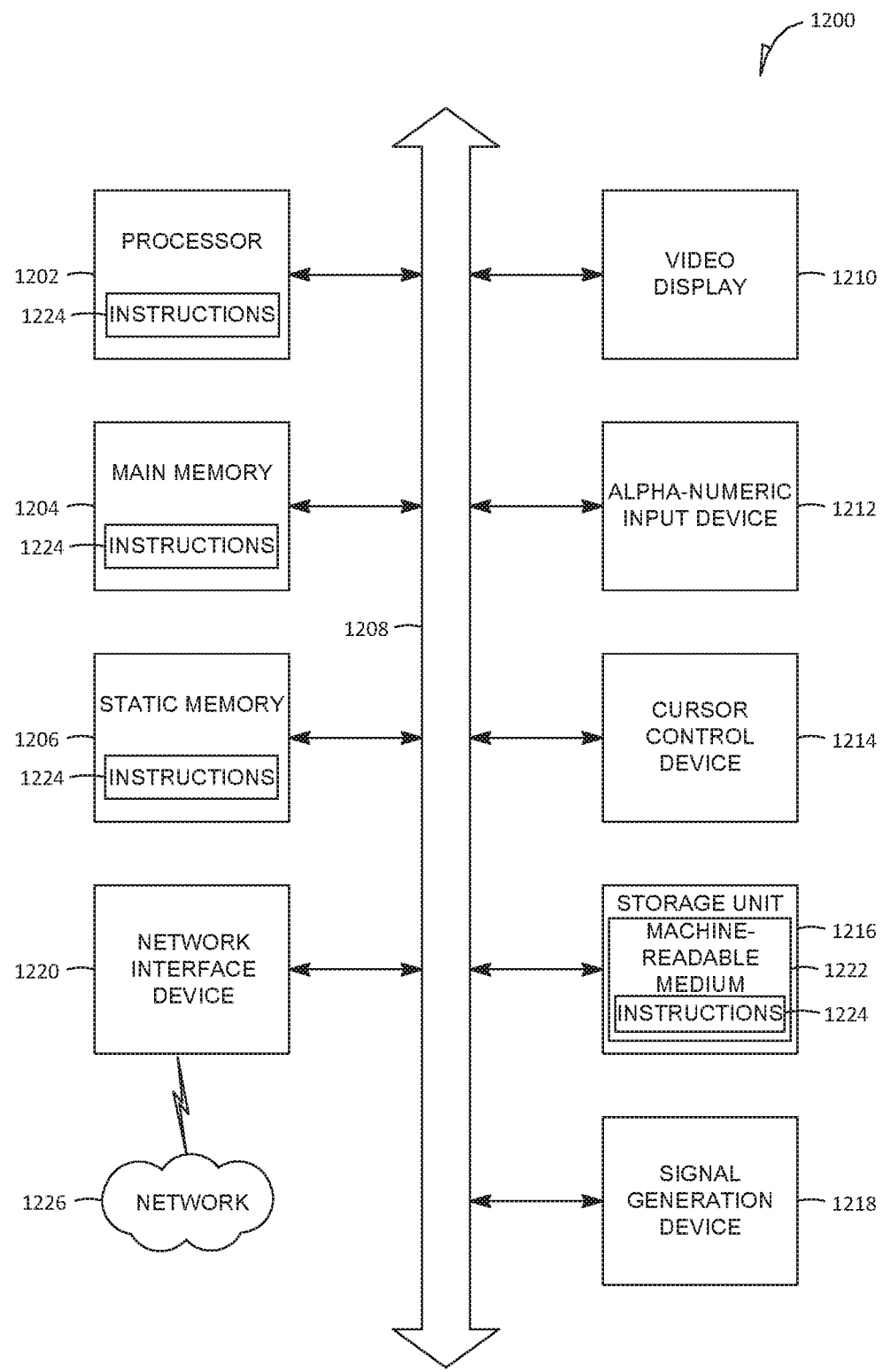
FIG. 19 is a block diagram of machine in the example form of a computer system within which instructions for causing the machine to perform one or more of the methodologies discussed herein may be executed.

FIG. 19 is a block diagram of machine in the example form of a computer system 1900 within which instructions for causing the machine to perform any one or more of the methodologies discussed herein may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a mobile phone (e.g., an iPhone or a mobile phone executing an Android operating system), a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1900 includes a processor 1902 (e.g., a central processing unit (CPU), a graphics processing unit (GPU) or both), a main memory 1904 and a static memory 1906, which communicate with each other via a bus 1908. The computer system 1900 may further include a video display unit 1910 (e.g., a liquid crystal display (LCD) or a cathode ray tube (CRT)). The computer system 1900 also includes an alphanumeric input device 1912 (e.g., a keyboard), a user interface (UI) navigation (or cursor control) device 1914 (e.g., a mouse), a disk drive unit 1916, a signal generation device 1918 (e.g., a speaker) and a network interface device 1920.

The disk drive unit 1916 includes a machine-readable medium 1922 on which is stored one or more sets of instructions and data structures (e.g., software) 1924 embodying or utilized by any one or more of the methodologies or functions described herein. The instructions 1924 may also reside, completely or at least partially, within the main memory 1904 and/or within the processor 1902 during execution thereof by the computer system 1900, the main memory 1904 and the processor 1902 also constituting machine-readable media. The instructions 1924 may also reside, completely or at least partially, within the static memory 1906.

While the machine-readable medium 1922 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present embodiments, or that is capable of storing, encoding or carrying data structures utilized by or associated with such instructions. The term "machine-readable medium" shall accordingly be taken to include, but not be limited to, solid-state memories, and optical and magnetic media, Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and compact disc-read-only memory (CD-ROM) and digital versatile disc (or digital video disc) read-only memory (DVD-ROM) disks.

The instructions 1924 may further be transmitted or received over a communications network 1926 using a transmission medium. The instructions 1924 may be transmitted using the network interface device 1920 and any one of a number of well-known transfer protocols (e.g., HTTP). Examples of communication networks include a LAN, a WAN, the Internet, mobile telephone networks, POTS networks, and wireless data networks (e.g., WiFi and WiMax networks). The term "transmission medium" shall be taken to include any intangible medium capable of storing, encoding or carrying instructions for execution by the machine, and includes digital or analog communications signals or other intangible media to facilitate communication of such software. The network 1926 may be one of the networks 120.

Although an embodiment has been described with reference to specific example embodiments, it will be evident that various modifications and changes may be made to these embodiments without departing from the broader scope of the present disclosure. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system comprising:
   one or more computer processors;
   one or more computer memories;
   a set of instructions incorporated into the one or more computer memories, the set of instructions configuring the one or more computer processors to perform operations comprising:
   storing, in a database of a persistence layer of a wellness system, information about online support groups to which members of the wellness system belong;
   laying out selected information from the information about the online support groups in a caching layer of the wellness system, the selected information selected to facilitate a clustering process, the selected information including participation levels of the members, the participation levels pertaining to structured interactions or unstructured interactions of the members;
   automatically performing the clustering process using the selected information laid out in the caching layer, the automatic performing of the clustering process comprising:
   based on a detecting of a change to group dynamics of the online support groups, determining an optimization for the online support groups, the optimization based on one or more optimization criteria, the one or more optimization criteria including the selected information laid out in the caching layer;
   determining a success of the optimization based on one or more measurement criteria, the one or more measurement criteria including a satisfaction of the members with the group dynamics; and
   modifying the online support groups based on the success of the optimization as new information is collected by the wellness system.

2. The system of claim 1, wherein the determining of the success of the optimization is based on a consistency of the members in logging meals with respect to the wellness system.

3. The method of claim 1, wherein the determining of the optimization is further based on a detecting of a change that pertains to a goal, a preference, or an attribute of one of the members.

4. The method of claim 1, wherein the modifying includes a promotion of one of the members to a facilitator role or a demotion of a facilitator to a member role.

5. The method of claim 1, wherein the modifying includes automatically moving one or more of the members between the online support groups.

6. The method of claim 1, wherein the modifying includes merging of two or more of the online support groups.

7. The method of claim 6, wherein the merging is based on permission of at least a subset of the members affected by the merging.

8. The method of claim 1, wherein the modifying is performed invisibly to the members.

9. A method comprising:
   storing, in a database of a persistence layer of a wellness system, information about online support groups to which members of the wellness system belong;
   laying out, in a caching layer of the wellness system, selected information from the information about the online support groups, the selected information selected to facilitate a clustering process, the selected information including participation levels of the members, the participation levels pertaining to structured or unstructured interactions of the members;
   automatically performing the clustering process using the selected information laid out in the caching layer, the automatic performing of the clustering process comprising:
   based on a detecting of a change to group dynamics of the online support groups, determining an optimization for the online support groups, the optimization based on one or more optimization criteria, the one or more optimization criteria including the selected information laid out in the caching layer;
   determining a success of the optimization based on one or more measurement criteria, the one or more measurement criteria including a satisfaction of the members with the group dynamics; and
   modifying the online support groups based on the success of the optimization as new information is collected by the wellness system.

10. The method of claim 9, wherein the determining of the success of the optimization is based on a consistency of the members in logging meals with respect to the wellness system.

11. The system of claim 9, wherein the modifying includes a promotion of one of the members to a facilitator role or a demotion of a facilitator to a member role.

12. The system of claim 9, wherein the modifying includes automatically moving one or more of the members between the online support groups.

13. The system of claim 9, wherein the modifying includes merging of two or more of the online support groups.

14. The system of claim 13, wherein the merging is based on permission of at least a subset of the members affected by the merging.

15. The system of claim 9, wherein the modifying is performed invisibly to the members.

16. A non-transitory machine readable storage medium storing a set of instructions that, when executed by at least one processor, causes the at least one processor to perform operations, the operations comprising:
   storing, in a database of a persistence layer of a wellness system, information about online support groups to which members of the wellness system belong;
   laying out selected information from the information about the online support groups in a caching layer of the wellness system, the selected information selected to facilitate a clustering process, the selected information including participation levels of the members, the participation levels pertaining to structured interactions or unstructured interactions of the members;
   automatically performing the clustering process using the selected information laid out in the caching layer, the automatic performing of the clustering process comprising:
   based on a detecting of a change to group dynamics of the online support groups, determining an optimization for the online support groups, the optimization based on one or more optimization criteria, the one or more optimization criteria including the selected information laid out in the caching layer;
   determining a success of the optimization based on one or more measurement criteria, the one or more measurement criteria including a satisfaction of the members with the group dynamics; and
   modifying the online support groups based on the success of the optimization as new information is collected by the wellness system.

17. The non-transitory machine readable storage medium of claim 16, wherein the determining of the success of the optimization is based on a consistency of the members in logging meals with respect to the wellness system.

18. The non-transitory machine readable storage medium of claim 16, wherein the modifying includes a promotion of one of the members to a facilitator role or a demotion of a facilitator to a member role.

19. The non-transitory machine readable storage medium of claim 16, wherein the modifying includes automatically moving one or more of the members between the online support groups.

20. The non-transitory machine readable storage medium of claim 16, wherein the modifying includes merging of two or more of the online support groups.

* * * * *